(12) United States Patent
Trombetta et al.

(10) Patent No.: US 6,177,605 B1
(45) Date of Patent: Jan. 23, 2001

(54) ABSORBENT COMPOSITE WEB

(75) Inventors: Liberatore A. Trombetta, Silvi; Dennis A. Darby, Pescara, both of (IT)

(73) Assignee: The Procter & Gamble Company, Cincinnati, OH (US)

( * ) Notice: Under 35 U.S.C. 154(b), the term of this patent shall be extended for 0 days.

This patent is subject to a terminal disclaimer.

(21) Appl. No.: 09/122,906

(22) Filed: Jul. 27, 1998

Related U.S. Application Data

(63) Continuation of application No. 08/867,094, filed on Jun. 2, 1997, now Pat. No. 5,785,697.

(51) Int. Cl.[7] .................................................. A61F 13/15
(52) U.S. Cl. .......................................... 604/378; 428/131
(58) Field of Search ................................... 604/378, 380, 604/383, 385.01; 428/131, 137

(56) References Cited

U.S. PATENT DOCUMENTS

| | | | |
|---|---|---|---|
| 3,620,894 | * 11/1971 | Oates | 604/278 |
| 4,960,477 | * 10/1990 | Mesek | 604/378 |
| 5,785,697 | * 7/1998 | Trombetta et al. | 604/378 |
| 5,961,506 | * 10/1999 | Guidotti et al. | 604/378 |

* cited by examiner

*Primary Examiner*—Dennis Ruhl
(74) *Attorney, Agent, or Firm*—Joan B. Tucker; Thomas J. Osborne, Jr.; David M. Weirich

(57) ABSTRACT

The present invention provides an absorbent composite web comprising a primary material having a top surface, a bottom surface, and a plurality of apertures extending from the top surface to the bottom surface. Furthermore, a secondary material is positioned adjacent to the primary material bottom surface. The secondary material extends into the plurality of apertures in the primary material.

21 Claims, 5 Drawing Sheets

ABSORBENT COMPOSITE WEB

This is a continuation of application Ser. No. 08/867,094, filed on Jun. 2, 1997, now U.S. Pat. No. 5,785,697.

FIELD OF THE INVENTION

The present invention provides an absorbent composite web comprising a fluid distributing, apertured primary material and an absorbent secondary material. The apertures of the primary material are substantially filled-in by the secondary material which may also cover the bottom surface of the primary material thereby producing a multi-layered, absorbent composite web.

BACKGROUND OF THE INVENTION

It has long been known in the disposable absorbent article art that it is extremely desirable to construct absorptive devices such as disposable diapers, catamenial pads, sanitary napkins, incontinence briefs, incontinence pads, and the like, which present a dry surface feel to the user for improving wearer comfort and to minimize the development of undesirable skin conditions due to prolonged exposure to moisture absorbed within the absorbent article. Accordingly, it is generally desirable to promote fluid transfer in a direction away from the wearer and into an absorbent element, while resisting fluid transfer in the reverse direction.

Conventional absorbent articles typically include an absorbent element (sometimes referred to as an absorbent core) interposed between a fluid pervious body-contacting element (sometimes referred to as a topsheet or an overwrap) and a fluid impervious protective barrier (sometimes referred to as a backsheet). The absorbent element is, of course, intended to receive and contain body fluids such as menses and urine. The body-contacting element is intended to provide more or less comfortable and dry-feeling contact with body surfaces while allowing free passage of fluids therethrough and into the absorbent element. The protective barrier is intended to prevent body fluids, which are expelled or which escape from the absorbent element, from soiling the user's garments.

The comfort of the user is enhanced if the absorbent article, in addition to its properties of high fluid transmisivity and fluid retention, exhibits the characteristic of uni-directional fluid transmisivity. This will improve what is known as the rewet characteristic of the absorbent product. Fluid should quickly and easily transmit through the topsheet and into the absorbent core. As the absorbent core becomes saturated, fluid will tend to pass back through the absorbent article, or rewet, causing user discomfort. As the absorbent core becomes increasingly saturated during use or is subjected to a pressure, there will be a tendency of the fluid to transmit back through the cover, or rewet the cover's surface and hence the body of the user. This discomfort caused by rewetting can cause the user to discard the absorbent product before its useful life has terminated. Therefore, it is desirable to inhibit such rewetting and thereby reduce user discomfort.

SUMMARY OF THE INVENTION

Accordingly, the invention provides an absorbent composite web comprising a primary material having a top surface, a bottom surface, and a plurality of apertures extending therethrough from the top surface to the bottom surface. Furthermore, a secondary material is preferably positioned adjacent to the primary material bottom surface whereby the secondary material extends into the plurality of apertures within the primary material.

In one application of the embodiment herein, the secondary material of the web may comprise from about 10 wt. % to about 90 wt. % of cellulosic material. In a further embodiment herein, the secondary material may comprise from about 10 wt. % to about 90 wt. % of synthetic material. A web herein preferably comprises a secondary material having both cellulosic material and synthetic material.

Preferably, the web herein comprises a primary material that may comprise bi-component fibers, monocomponent fibers, tri-component fibers or a combination of all three.

In a particularly preferred embodiment herein, the primary material may further comprise a wetting agent, e.g., a surfactant, to more efficiently draw fluid away from a user and/or the top surface of the primary material. Also preferably, the secondary material may comprise an element selected from the group consisting of absorbent gelling material, superabsorbent polymers, silica, perfume, cyclodextrins, zeolite, charcoal, silica, cyclodextrins and combinations thereof.

In an alternative embodiment herein, the web may further comprise a tertiary material having a top surface placed immediately adjacent to the bottom of the secondary material.

In one embodiment of the invention herein, a disposable diaper comprises a chassis having an upper surface and a bottom surface, a front portion, a back portion positioned opposite to the front portion, a crotch portion positioned between the front portion and the back portion, a longitudinal axis, a transverse axis, a pair of end edges being parallel to the transverse axis and a pair of longitudinal edges being parallel to the longitudinal axis. The chassis further comprises a topsheet and a backsheet joined to the topsheet. The backsheet has an inner surface and an outer surface. A fluid handling member is positioned between the topsheet and the backsheet. The fluid handling member comprises a primary material having a top surface, a bottom surface, and a plurality of apertures extending from the top surface of the primary material to its bottom surface. Furthermore, a secondary material is positioned adjacent to the primary material bottom surface. The secondary material extends into the plurality of apertures in the primary material.

The fluid handling member may comprise at least a portion of the topsheet and/or the absorbent core. Also, if there is a separate topsheet and/or absorbent core, the fluid handling member is preferably positioned between and placed adjacent to the topsheet and the absorbent core, respectively.

BRIEF DESCRIPTION OF THE DRAWINGS

While the specification concludes with claims particularly pointing out and distinctly claiming the subject matter which is regarded as forming the present invention, it is believed that the invention will be better understood from the following descriptions which are taken in conjunction with the accompanying drawings in which like designations are used to designate substantially identical elements, and in which:

DETAILED DESCRIPTION OF THE INVENTION

As used herein, the term "absorbent article" refers to devices which absorb and contain body exudates, and, more specifically, refers to devices which are placed against or in close proximity to the body of the wearer to absorb and contain the various exudates discharged from the body. The term "disposable" is used herein to describe absorbent articles which are not intended to be laundered or otherwise restored or reused as an absorbent article (i.e., they are intended to be discarded after a single use, and, preferably, to be recycled, composted or otherwise disposed of in an environmentally compatible manner). A "unitary" absorbent article refers to absorbent articles which are formed of separate parts united together to form a coordinated entity so that they do not require separate manipulative parts like a separate holder and pad.

Figure 1:
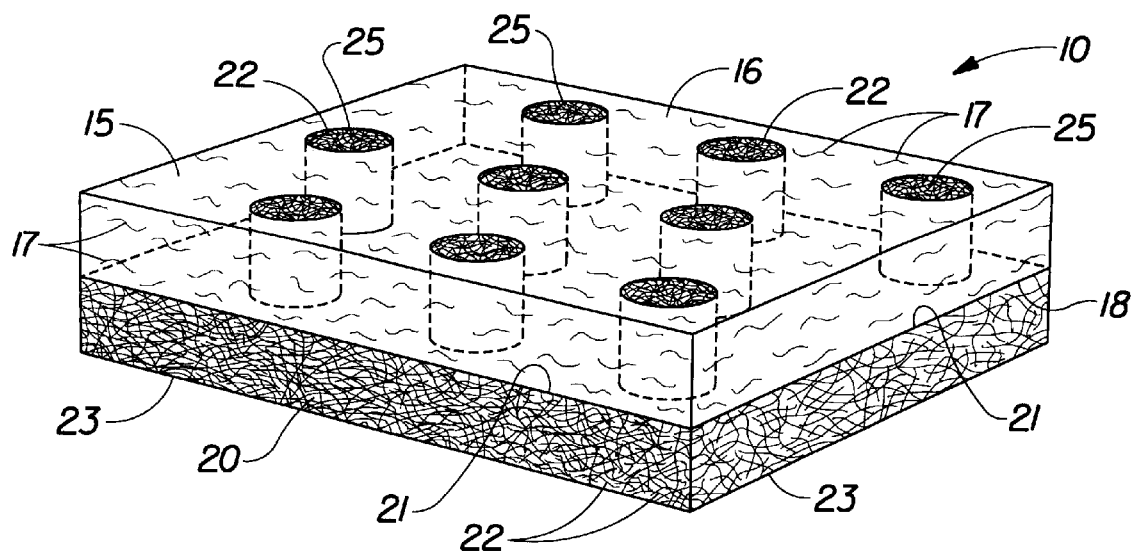
FIG. 1 is a perspective view of the absorbent composite web of the present invention.

FIG. 1 provides a perspective view of a web 10 or absorbent composite web 10. By the terms "web" and "absorbent composite web" it is meant herein a multi-layered absorbent or fluid transporting and retaining structure made of two or more distinct parts where at least one part of the structure functions primarily to transport fluid. The web 10 preferably comprises a primary material 15 formed by a first set of fibers 17. The primary material 15 comprises a top surface 16 which preferably faces toward a user when the web 10 is utilized in a disposable absorbent article. Opposite of the top surface 16 is the bottom surface 18 of the primary material 15. As is seen in FIG. 1, the primary material 15 is formed in such a way as to provide apertures 25 throughout the primary material 15. These apertures 25 extend from the top surface 16 to the bottom surface 18 of the primary material 15. The apertures 25 may be randomly assigned throughout the primary material 15 or they may be located in any organized or regular configuration conceivable throughout the primary material 15. Preferably, the apertures 25 will be regularly shaped from top to bottom. Also, the apertures 25 may comprise a wider opening at the top surface 16 than at the bottom surface 18 and the reverse also is true.

The secondary material 20 is formed from a second set of fibers 22. The secondary material comprises an upper surface 21 and a lower surface 23. The upper surface 21 of the secondary material 20 is positioned adjacent to the bottom surface 18 of primary material 15. As is clearly seen in FIG. 1, the secondary material 20 not only forms a layer that is adjacent to the bottom surface 18 of the primary material 15, but also is inserted within the apertures 25 of the primary material 15. Therefore, as fluid insults the top surface 16 of the primary material 15, it will also immediately insult at least a portion of the secondary material 20, i.e., those portions within the apertures 25.

FIG. 1 provides a view in which the secondary material 20 located within the apertures 25 appears to be at equal level to the top surface 16 of the primary material 15. This is a preferred embodiment, however, the secondary material 20 may extend from about one-fourth from the base of an aperture 25 to about the total height of an aperture 25. However, for premium performance, it is believed herein that the level of the secondary material 20 within an aperture 25 should be approximately equal to the top surface 16 of the primary material 15.

Preferably, the first set of fibers 17 used to form the primary material 15 are moisture insensitive. By the term "moisture insensitive" it is meant herein that the fibers will substantially not absorb any fluid within its structure and further will not collapse as a result of fluid insult. Furthermore, the fibers 17 will remain intact upon liquid insult and most importantly will not retain any liquid. The objective of the fibers 17 is to collect fluid quickly and transport it just as quickly out of its structure to the fibers 22 of the secondary material 20 for storage. To further accommodate this transport function of the primary material 15, the density of the primary material 15 should be less than the density of the secondary material 20.

While the density of the primary material 15 is preferably less than the density of the secondary material 20, it should be noted that the void volume, which is the inverse of density herein, is preferably higher for the primary material 15 than for the secondary material 20. In practice, void volume relates to the amount of voids or spaced volume (i.e., spaces) per gram of fibers. It is desirable that there be more open spaces in the primary material 15 than the secondary material 20 to create a density gradient across the two materials whereby fluid is readily and quickly suctioned from the primary material to the secondary material. As has been noted above, the primary material 15 is to be fashioned in such a way as to enable its structure to quickly receive fluids and then transport them to the secondary material 20 without the collapse of the primary material 15. In this fashion, the primary material 15 will then be able to receive multiple fluid insults and then transfer such fluids to the secondary material 20.

Generally, because the material within apertures 25 and the secondary layer positioned below the primary layer comprise the same fibers, i.e., the second set of fibers 22, each will have approximately the same density. However, either the material within apertures 25 or the secondary material layer positioned below the primary layer may be further densified through compaction or the addition of certain elements which may include, but are not limited to, absorbent gelling material, superabsorbent polymers, silica, perfume, cyclodextrins, absorbent foam, thermobondable fibers, charcoal, zeolite etc. For example, in one embodiment, the secondary material may be densified by elements which then cause it to have a greater density than both the primary material 15 and the material within apertures 25. In such an embodiment, density gradients are established across the primary material 15 to the secondary material 20 as well as across the material within apertures 25 to the secondary material 20; this is a preferred embodiment.

Also, the material within apertures 25 may be made to be more dense than the secondary material 20.

In an alternative embodiment herein, the densities for each component of the web 10 may have densities which are all approximately equal. In such a case, there is little or no discernible density gradient established across the primary material 15, the secondary material 20 or the material within apertures 25.

Preferably, the secondary material 20 will have a greater basis weight than the primary material 15. This corresponds to the secondary material 20 also preferably having the greater density than the primary material 15 and helps to ensure that a density gradient from the primary material 15 to the secondary material 20 is established.

The calipers for both the primary material 15 and the secondary material 20 are in the ranges of 0.5 to 10 mm, preferably 1 to 5 mm and more preferably 1.5 to 2.0 mm. The basis weights for the primary material 15 and the secondary material 20 are in the ranges of 20–3000 g/m$^2$, preferably 40–1000 g/m$^2$ and more preferably 50–300 g/m$^2$.

In an alternative embodiment herein, density gradients are created within either the primary material 15, the secondary material 20 or both. When a density gradient is established within the primary material 15, it relates also to the varying pore sizes established throughout the primary material 15 and is thus also referred to as the pore size gradient. The density within the primary material 15 may be made to be less dense towards its top surface 16 and more dense towards the upper surface 21 of the secondary material 20, i.e., the bottom surface of the primary material 15. This inner densification may be performed by compacting the fibers within the primary material 15 and/or through forming the primary material 15 from like or similar fibers of varying denier, i.e., the coarseness or fineness of a fiber.

In like fashion, the secondary material 20 may be inner denisified whereby the portion of the material 20 closest to the upper surface 21 is less dense than the portion nearest to the lower surface 23 of the secondary material 20. Again, this inner densification may be performed through compaction of the fibers within the secondary material 20 and/or through forming the secondary material 20 from like or similar fibers of varying denier, i.e., the coarseness or fineness of a fiber.

The varying denier of the fibers within a material establishes the density or pore size gradient within the materials. Preferably, higher denier fibers, which correspond to coarser fibers, will reside closest to the top and upper surfaces of the primary and secondary materials. Lower denier fibers will then therefore preferably reside closest to the lower or bottom surfaces of the primary and secondary materials. Such preferred construction creates primary and secondary materials that are less dense at their upper surfaces and more dense at their lower surfaces. Specifically, the coarser upper fibers (i.e., those having higher deniers) are more resilient and less structurally compressive and thus allow for the creation of greater void volumes in the upper surfaces of a material. Finer upper fibers (i.e., those having lower deniers) are less resilient and more structurally compressive and thus allow for the creation of greater compaction and fewer void volumes in the lower surfaces of a material. It is preferred herein that the lower or bottom portion of a material be more dense and that their upper portions be less dense to receive fluids quickly, thereby pulling them away from the top surfaces and holding them within the lower surfaces of a material away from its upper surfaces.

Figure 7:
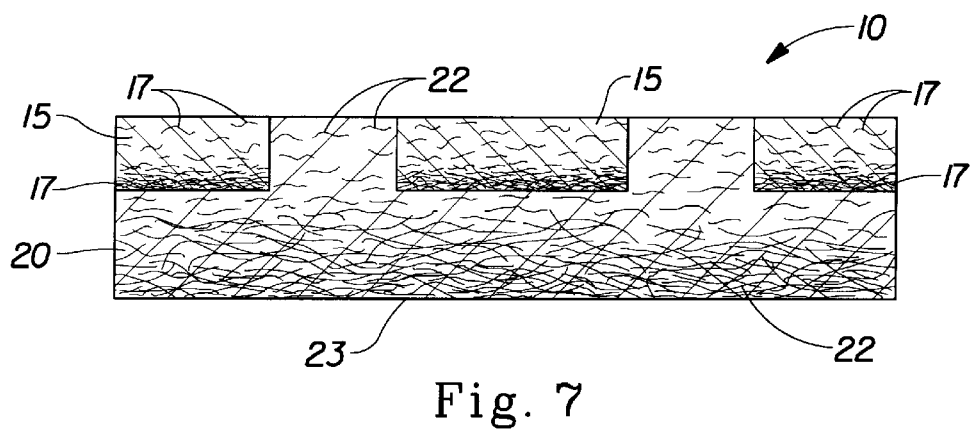
FIG. 7 is a cross-sectional view of an alternative embodiment of the absorbent composite web of the present invention.

FIG. 7 shows a cross-sectional view of a web 10 having primary material 15 and a secondary material 20 that have been inner densified with fibers 17 and fibers 22, respectively. As has been mentioned above, this inner densification may have occurred either through compaction of the fibers and/or through the inclusion of fibers of varying deniers. It should be noted herein that though the primary material 15, for example, may comprise fibers 17 of varying deniers, the basis weights of the fibers are all approximately equal. That is, the basis weights of the fibers do not vary as the denier of the fibers within a material varies. It is further noted that the inner densification of fibers may occur by the use of varying fiber types having different weights, thicknesses, bulk densities and other attributes that may affect density within the materials 15 and 20.

The primary material 15 may also be formed from a nonwoven web which may be a spunbonded web, a meltblown web, a bonded carded web, or a thermally bonded airlaid web. The nonwoven web may be made of fiber forming polymers such as, for example, polyesters, polyamines, and polyolefins. Exemplary polyolefins include one or more of polypropylene, polyethylene, ethylene copolymers, propylene copolymers, and butene copolymers.

In another preferred embodiment, the nonwoven web may comprise bicomponent fibers. The bicomponent fiber used herein is preferably a thermobondable bicomponent fiber having an inner core component and outer sheath component where the inner core component has a higher melting point than the outer sheath component. The fiber is typically hydrophobic, but can be made hydrophilic by incorporating a surfactant into the sheath of the bicomponent fiber and/or by treating the external surface of the sheath with a surfactant. Exemplary bicomponent fibers and processes for producing the same are described in U.S. Pat. No. 5,456,982 entitled "Bicomponent Synthesis Fibre And Process For Producing Same", issued to Hansen et al. on Oct. 10, 1995 and U.S. Pat. No. 5,603,707 entitled "Absorbent Article Having A Rewet Barrier", issued to Trombetta et al. on Feb. 18, 1997, each of which patents are incorporated herein by reference. Whatever bicomponent fiber is used herein, it must be substantially moisture insensitive so as not to absorb an amount of fluid that would either hinder rewet of the primary material 15 or cause the structural integrity of the primary material 15 to collapse or be otherwise compromised.

The primary material 15 should have an operable level of density and basis weight to rapidly acquire and then drain liquid surges into the underlying secondary material 20, thus remaining substantially empty to receive subsequent liquid surges, i.e., insults. The primary material 15 should have sufficient void volume capacity to temporarily retain the amount of liquid that is typically discharged by a wearer during a single insult or surge of liquid into the web 10. Insufficient void volume capacity may result in excessive pooling of liquid against the wearer's skin or excessive run-off of liquid. It should be noted herein that the primary material 15 preferably comprises substantially no cellulosic material or any type of absorbent fiber that would retain and not substantially transfer all of the fluid received by the primary material 15 to the secondary material 20 and/or the fibers 22 within an aperture 25.

The secondary material 20 preferably comprises from about 10 wt. % to about 90 wt. % of cellulosic material and from about 10 wt. % to about 90 wt. % of synthetic material. More preferably, the secondary material 20 comprises from about 10 wt. % of a synthetic fiber like polyolefin to about 90 wt. % of a cellulosic fiber like wood pulp or rayon. The purpose for the secondary material 20 is to create an absorbent, fluid-retaining structure for the fluid transported to the secondary material 20 by the primary material 15. This is especially true where the web 10 is the only or primary fluid absorbing and retaining structure in an absorbent article.

Suitable absorbent materials for use in the secondary material 20 are comminuted wood pulp which is generally referred to as airfelt, creped cellulose wadding; meltblown polymers including coform; chemically stiffened, modified or cross-linked cellulosic fibers; synthetic fibers such as crimped polyester fibers, polyester, polyamines and polyolefin; peat moss; tissue including tissue wraps and tissue laminates; absorbent foams; absorbent sponges; superabsorbent polymers; absorbent gelling materials; or any equivalent material or combinations of materials, or mixtures of these.

Figure 2:
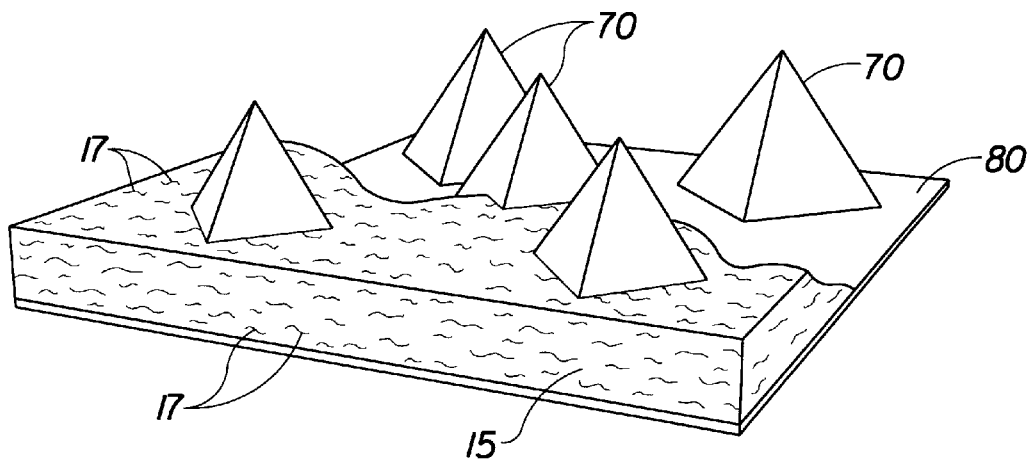
FIG. 2 is a perspective view of a portion of a patterned screen used in a process for the forming of a primary material.
Figure 3A:
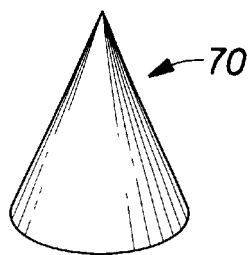
FIG. 3A is a perspective view of an alternative embodiment of a raised portion.
Figure 3B:
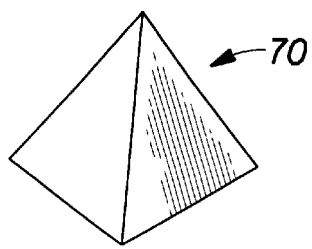
FIG. 3B is a perspective view of an alternative embodiment of a raised portion.
Figure 3C:
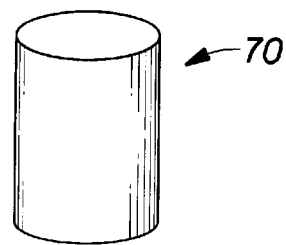
FIG. 3C is a perspective view of an alternative embodiment of a raised portion.

FIG. 2 provides a perspective view of a section of the forming process for the web 10. Specifically, a first set of fibers 17 for the primary material 15 are shown being laid down onto a patterned screen 80 having alternating raised portions 70 throughout. FIG. 2 shows the patterned screen 80 being partially filled with fibers 17, but in practice, such a screen 80 would be completely filled across with the fibers 17. Furthermore, the raised portions 70 are shown to be pyramidal in shape. However, as is shown in FIGS. 3A, 3B and 3C, the raised portions may be in any shape desired by a manufacturer, e.g., pyramidal, conical, cylindrical, polygonal, spherical, etc., to produce a desired shaped aperture 25, e.g., apertures having conical, pyramidal, polygonal, cylindrical, spherical, etc. types of shapes. It is noted herein that several types of raised portions 70 may be used on one patterned screen 80. The type of raised portion 70 used will depend on the desired shape, contour and structure of apertures within the primary material 15.

Figure 4:
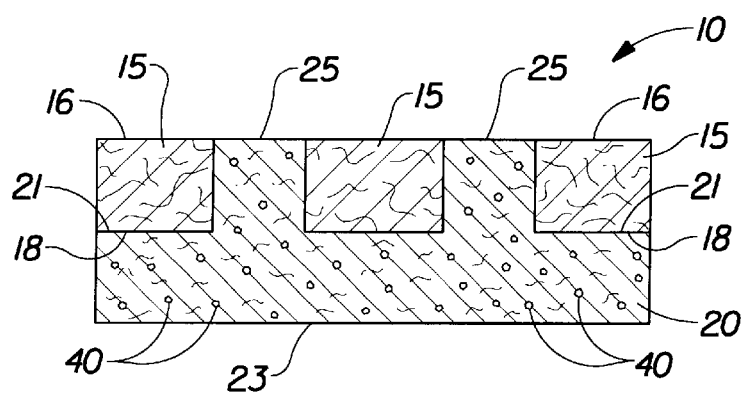
FIG. 4 is a cross-sectional view of an absorbent composite web of the present invention.
Figure 4A:
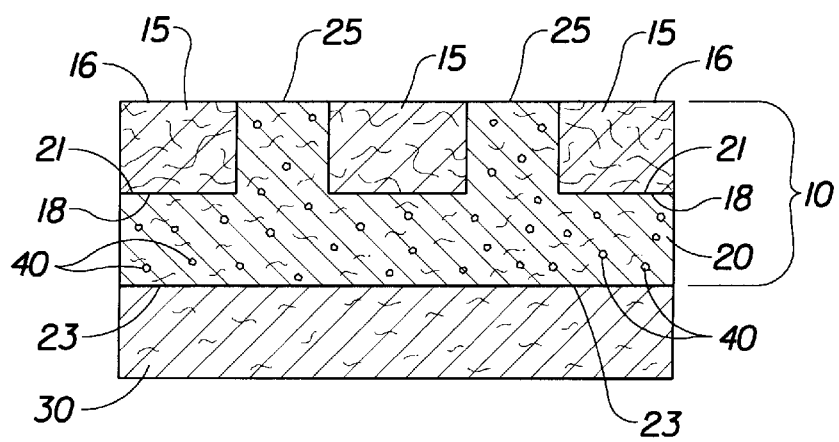
FIG. 4A is a cross-sectional view of an alternative embodiment of an absorbent composite web of the present invention.

FIGS. 4 and 4A show cross-sections of two webs 10. Both figures show the primary material 15 and the secondary material 20. FIG. 4A shows an additional absorbent material 30 positioned adjacent to the bottom surface of the secondary material 20. FIG. 4A represents an alternative embodiment herein wherein additional absorbent material is placed adjacent to the web 10. The absorbent material 30 may be the same as or similar to the absorbent material used in the secondary material 20. In an absorbent article embodiment, absorbent material 30 may represent an absorbent core (e.g., the absorbent core 540 of FIG. 5).

In another preferred embodiment herein, both the primary and secondary materials may substantially and/or fully comprise an absorbent and/or fluid-acquiring foam. For the structures disclosed in the present invention, the primary material may comprise a substantially fluid-acquiring and fluid-distributing foam while the secondary material may comprise a substantially fluid absorbing and retaining foam, each of which materials preferably being a functional absorbent material. Suitable examples of functional absorbent materials herein are disclosed in U.S. Pat. No. 5,387,207 issued to Dyer, et al., U.S. Pat. No. 5,563,179 issued to DeMarais, et al., and U.S. patent application Ser. No. 08/370,922 (DesMarais, et al.) entitled "Absorbent Foam Materials For Aqueous Fluids Made From High Internal Phase Emulsions Having Very High Water To Oil Ratios" and 08/484,727 (DesMarais, et al.) entitled "Foam Materials For Insulation Derived From High Internal Phase Emulsions", all of which references are incorporated by reference.

Where fluid-acquiring and absorbing foams are used for the web 10, the structure of web 10 will be similar to that portrayed in FIG. 1. Specifically, the fluid-acquiring layer would be the primary material 15, and the fluid-absorbing layer would be the secondary material 20. In one embodiment the web 10 comprising the fluid-acquiring and absorbent foams mentioned above will substantially comprise no fibers or additives (e.g., charcoal, perfume, etc.). In another embodiment the web 10 comprising the fluid-acquiring and absorbing foams may comprise fibers and/or additives.

Also disclosed in FIGS. 4 and 4A are additives or elements included within the secondary material 20. The elements 40 may be materials responsible for added fluid absorption, odor control, fragrance release, etc. These elements may be selected from a group consisting of absorbent gelling material, zeolite, charcoal, silica, cyclodextrins, thermobondable fibers, perfume and combinations thereof.

It is further noted herein that the web 10 may comprise as many levels or layers of material as is desired by a manufacturer. In fact, multiple layers, i.e., at least two, of differing types of fibers with varying deniers, basis weights, and material calipers may be employed as part of the invention herein.

Figure 8:
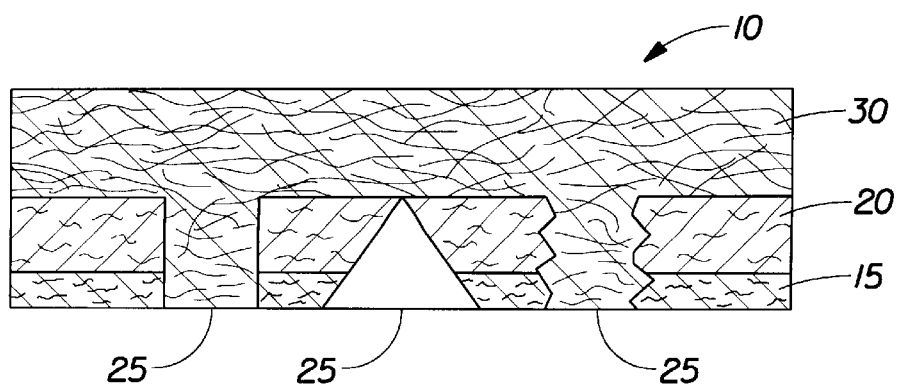
FIG. 8 is a cross-sectional view of an alternative embodiment of the absorbent composite web of the present invention.

FIG. 8 discloses an alternative embodiment herein where a web 10 comprises multiple layers or levels of materials. A primary material 15 sits adjacent to a secondary material 20 which sits adjacent to a tertiary material 30. Also, apertures 25 of varying shapes are fitted within the primary and secondary materials and lead to the tertiary material 30. These apertures 25 may either be filled with an absorbent material from fibers similar to those in the materials underlying the primary material 15, and/or the apertures 25 may be unfilled and thus serve as an immediate conduit to materials underlying the primary material 15. For example, the central aperture of the web 10, i.e., that aperture 25 having the pyramidal or conical shape, is substantially not filled with any fibers, absorbent or otherwise. This would serve to allow fluid to enter directly into the secondary material 20 and the tertiary material 30 as fluid impacts an unfilled aperture 25. It is noted herein that the fibers within the apertures 25 of FIG. 8 are shown as fibers from the tertiary material 30, however, these fibers may also be from the secondary material 20. It is further noted herein that any of the elements mentioned herein (e.g., perfume, odor absorbers, etc.) may also be positioned within the secondary material 20 and/or the tertiary material 30 of the web 10 of FIG. 8.

A combination of unfilled and filled apertures 25 may be used in bi-layer and multi-layered absorbent composite webs 10 herein. By the term "multi-layered" it is meant a composite web herein having at least two material levels within its structure.

Suitable odor controlling and/or perfume agents are disclosed in U.S. Pat. No. 5,591,146 issued to Hasse on Jan. 7, 1997 and U.S. patent applications Ser. No. 08/635,221 filed on Apr. 17, 1996, entitled "Absorbent Article With Odor Masking Agents Released By The Fastening System" and U.S. patent applications Ser. No. 08/764,817 filed on Dec. 12, 1996, entitled "A Diaper Having Perfume Zones", each of which is incorporated herein by reference.

Figure 9:
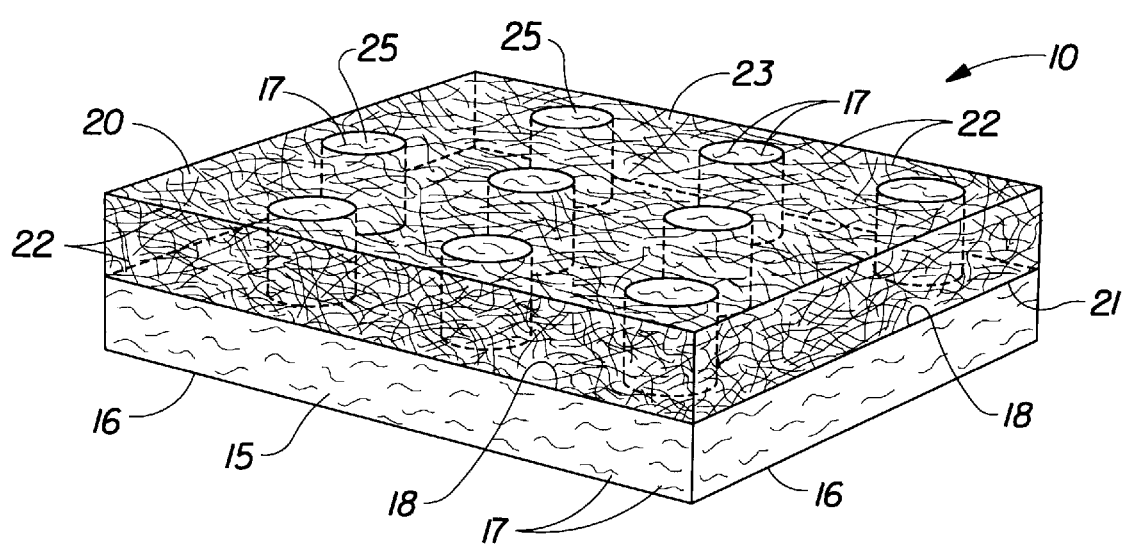
FIG. 9 is a perspective view of an alternative embodiment of the absorbent composite web of the present invention.

FIG. 9 discloses an alternative embodiment wherein the apertures 25 extend from the upper surface 21 to the lower surface 23 of the secondary material 20. This is a reversal of the structure of web 10 in FIG. 1. Additionally, the fibers 17 within the apertures 25 are those fibers that make up the primary material 15. The web 10 of FIG. 9 is shown upside down whereby the lower surface 23 of the secondary material is shown facing upwards. This view of the web 10 is meant to clearly indicate the apertures 25 and the fibers 17 that are located therein. In practice, the primary material of FIG. 9 is that material facing towards a user and the secondary material faces away from a user.

While not wishing to be bound by any particular theory, it is believed herein that as fluid is acquired at the top surface 16 of the primary material 15 in FIG. 9, the fluid will travel through the apertures 25 along the fibers 17 and either into an underlying absorbent element or into the secondary material 20 for storage. It is noted herein that the web 10 of FIG. 9 is not a stand alone structure like the web 10 in FIG. 1. That is, there must be an accompanying absorbent element placed adjacent to or nearly adjacent to the lower surface 23 of the secondary material 20. It is not the intention of any embodiment herein to allow the flow of fluid through an absorbent composite web 10 herein without its capture and storage.

The Disposable Diaper

Figure 5:
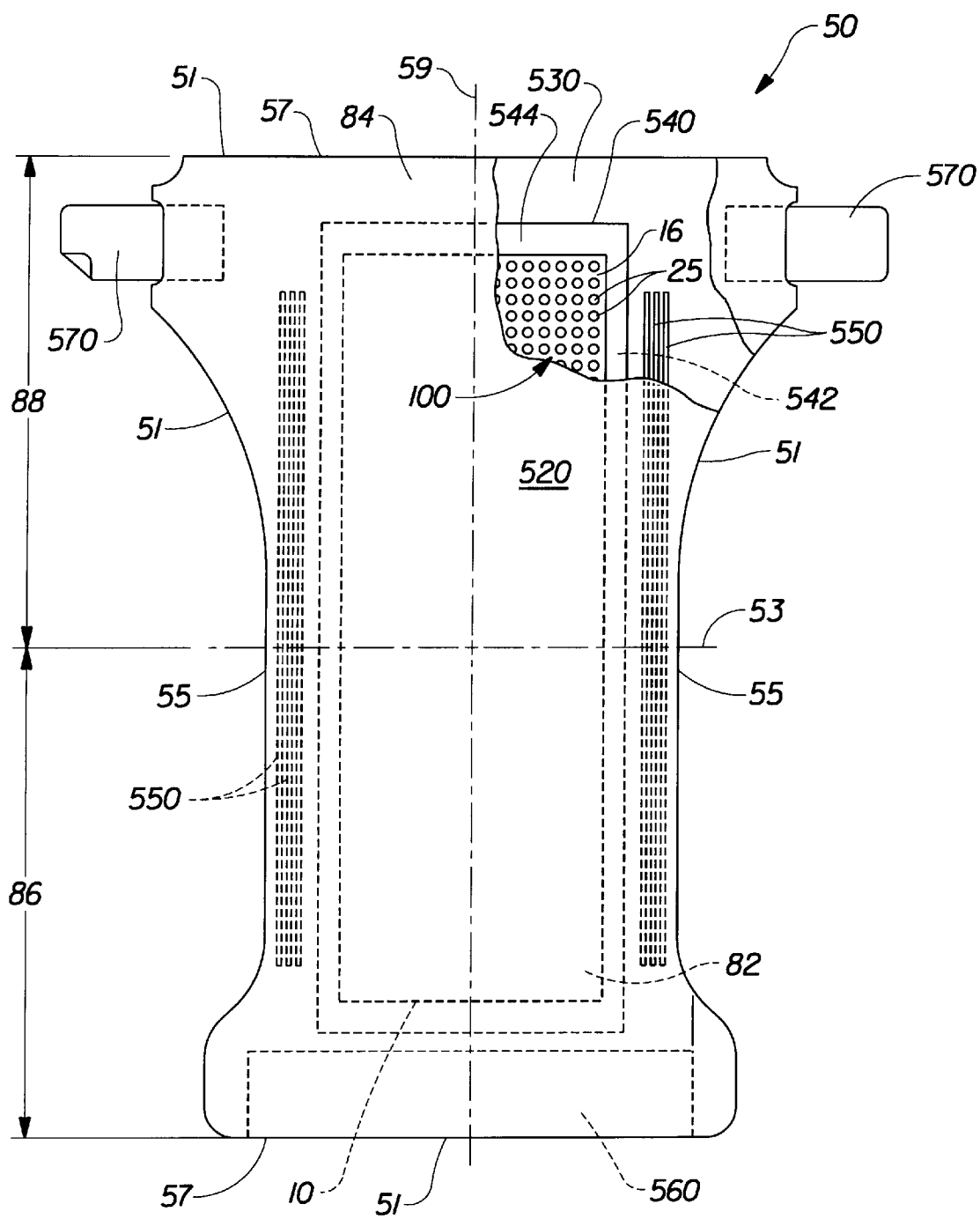
FIG. 5 is a plan view of a diaper embodiment employing a fluid handling member of the present invention.
Figure 6:
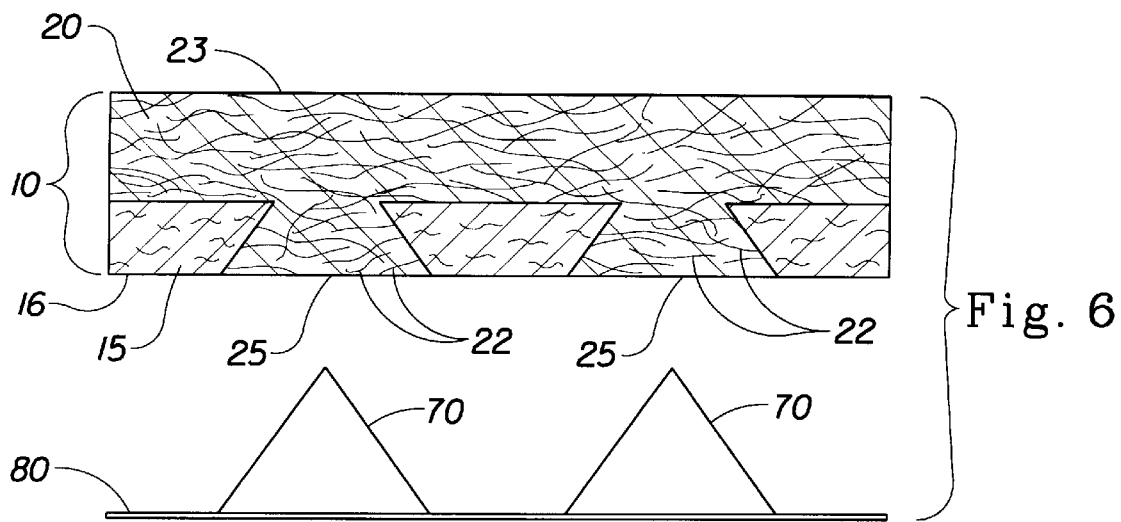
FIG. 6 is a cross-sectional view of a web forming process of the absorbent composite web of the present invention.

A preferred embodiment of the unitary disposable absorbent article of the present invention is the diaper 50 shown in FIG. 5. As used herein, the term "diaper" refers to an absorbent article generally worn by infants, and incontinent persons that is worn about the lower torso of the wearer. In other words, the term "diaper" includes infant diapers, training pants, adult incontinence devices, etc. However, it should be readily seen by one of skill in the art that the invention herein may be applied to other absorbent articles such as sanitary napkins, tampons, and interlabial devices.

The diaper 50 of the present invention, as shown in FIG. 5, comprises a liquid impervious backsheet 530 and a liquid pervious topsheet 520 joined to the backsheet 530. The topsheet 520 has a bottom surface (not shown) positioned away from a wearer and an upper surface oriented toward the skin of the wearer when the diaper 50 is being worn. Furthermore, an absorbent core 540 is positioned between the topsheet 520 and the backsheet 530.

FIG. 5 provides a plan view of the diaper 50 of the present invention in its flat-out, uncontracted state (i.e., with elastic induced contraction pulled out) with portions of the structure being cut-away to more clearly show the construction of the diaper 50 and with the portion of the diaper 50 which faces away from the wearer, the upper surface, oriented towards the viewer. As shown in FIG. 5, the diaper 50 preferably comprises a liquid pervious topsheet 520; a liquid impervious backsheet 530 joined with the topsheet 520; an absorbent core 540 positioned between the topsheet 520 and the backsheet 530, the absorbent core 540 having a garment facing surface 542 and a body facing surface 544 laying oppositely of the garment facing surface 542. The diaper 50 preferably further comprises elasticized leg cuffs 550; an elastic waist feature multiply designated as 560; and a fastening system generally multiply designated as 570.

The diaper in FIG. 5 further discloses a fluid handling member 100 positioned between the topsheet 520 and the backsheet 530. The fluid handling member 100 (or web 10 of FIG. 1) comprises a primary material 15 having a top surface 16, a bottom surface 18 (FIG. 1), and a plurality of apertures 25 extending from the top surface 16 to the bottom surface 18 of the primary material 15. A secondary material 20 (FIG. 1) is positioned adjacent to the primary material bottom surface 18. The secondary material 25 extends into the plurality of apertures 25 in the primary material 15. The fluid handling member 100 herein is of the same type and structure as the web 10 previously described herein.

In all embodiments herein where an absorbent core 540 and topsheet 520 are used, the fluid handling member 100 will be positioned between the body facing surface 544 of the absorbent core 540 and the topsheet bottom surface. When a topsheet 520 and an absorbent core 540 are both employed within the diaper 50, the fluid handling member 100 will be positioned directly adjacent to the topsheet bottom surface and the body facing surface 544 of the absorbent core 540. Further, the top surface 16 of the primary material 15 is placed adjacent to the topsheet bottom or garment surface while the bottom surface of the secondary material is placed adjacent to the body facing surface 544 of the absorbent core 540. In an alternative embodiment herein, the top surface 16 of the primary material 15 may at least be partially embedded with the topsheet 520 and may also serve as the portion of the topsheet 520 that is held directly against a user. Correspondingly, the bottom surface of the secondary material 20 may be embedded at least partially within the backsheet 530. Most preferably, the fluid handling member 100 is attached to the topsheet 520 and/or to the backsheet 530 to prevent shifting of the fluid handling member 100 within the diaper 50. Suitable attachment means for attaching the fluid handling member 100 to either the topsheet 520, absorbent core 540, backsheet 530, or to a combination of these may be adhesives, ultrasonic bonding, thermal bonding, dynamic mechanical bonding, crimping or a combination of any of these attachment means.

The diaper 50 is shown in FIG. 5 to have an outer surface 82, an inner surface 84 opposed to the outer surface 82, a first waist region 86, a second waist region 88, and a periphery 51 which is defined by the outer edges of the diaper 50 in which the longitudinal or side edges are designated 55 and the end edges are designated 57. (While the skilled artisan will recognize that a diaper is usually described in terms of having a pair of waist regions and a crotch region between the waist regions, in this application, for simplicity of terminology, the diaper 50 is described as having only waist regions including a portion of the diaper which would typically be designated as part of the crotch region). The inner surface 84 of the diaper 50 comprises that portion of the diaper 50 which is positioned adjacent to the wearer's body during use (i.e., the inner surface 84 generally is formed by at least a portion of the topsheet 520 and other components that may be joined to the topsheet 520). The outer surface 82 comprises that portion of the diaper 50 which is positioned away from the wearer's body (i.e., the outer surface 82 generally is formed by at least a portion of the backsheet 530 and other components that may be joined to the backsheet 530). (As used herein, the portion of the diaper 50 or components thereof which faces the wearer is also referred to as the body facing surface. Similarly, the portion facing away from the wearer is also referred to herein as the garment facing surface.) The first waist region 86 and the second waist region 88 extend, respectively, from the end edges 57 of the periphery 51 to the lateral centerline 53 of the diaper 50. FIG. 5 also shows the longitudinal centerline 59.

FIG. 5 shows a preferred embodiment of the diaper 50 in which the topsheet 520 and the backsheet 530 have length and width dimensions generally larger than those of the absorbent core 540. The topsheet 520 and the backsheet 530 extend beyond the edges of the absorbent core 540 to thereby form the periphery 51 of the diaper 50.

Diapers of the present invention can have a number of well known configurations, with the absorbent cores thereof being adapted to the present invention. Exemplary configurations are described generally in U.S. Pat. No. 3,860,003 issued to Buell on Jan. 14, 1975; U.S. Pat. No. 5,151,092 issued to Buell et al. on Sep. 29, 1992; U.S. Pat. No.

5,221,274 issued to Buell et al. on Jun. 22, 1993. Each of these patents is incorporated herein by reference. Another diaper configuration to which the present invention can be readily adapted are described in co-pending U.S. patent application Ser. No. 08/203,456; filed on Feb. 28, 1994 and incorporated herein by reference. The absorbent cores of diapers described in these patents can be adapted in light of the teachings herein to include the absorbent composite web of the present invention.

A topsheet 520 which is particularly suitable for use in the diaper 50, is carded and thermally bonded by means well known to those skilled in the fabrics art. A satisfactory topsheet for the present invention comprises staple length polypropylene fibers having a denier of about 2.2. As used herein, the term "staple length fibers" refers to those fibers having a length of at least about 15.9 mm (0.625 inches). Preferably, the topsheet has a basis weight from about 14 to about 25 grams per square meter. A suitable topsheet is manufactured by Veratec, Inc., a Division of International Paper Company, of Walpole, Mass. under the designation P-8.

The topsheet 520 of diaper 50 is preferably made of a hydrophilic material to promote rapid transfer of liquids (e.g., urine) through the topsheet. If the topsheet is made of a hydrophobic material, at least the upper surface of the topsheet is treated to be hydrophilic so that liquids will transfer through the topsheet more rapidly. This diminishes the likelihood that body exudates will flow off the topsheet rather than being drawn through the topsheet and being absorbed by the absorbent core. The topsheet can be rendered hydrophilic by treating it with a surfactant. Suitable methods for treating the topsheet with a surfactant include spraying the topsheet material with the surfactant and immersing the material into the surfactant. A more detailed discussion of such a treatment and hydrophilicity is contained in U.S. Pat. No. 4,988,344 entitled "Absorbent Articles with Multiple Layer Absorbent Layers" issued to Reising, et al on Jan. 29, 1991 and U.S. Pat. No. 4,988,345 entitled "Absorbent Articles with Rapid Acquiring Absorbent Cores" issued to Reising on Jan. 29, 1991, each of which is incorporated by reference herein.

In a preferred embodiment of a diaper as described herein, the backsheet 530 has a modified hourglass shape extending beyond the absorbent core a minimum distance of about 1.3 cm to about 6.4 cm (about 0.5 to about 2.5 inch) around the entire diaper periphery.

The absorbent core 540 may take on any size or shape that is compatible with the diaper 50. One preferred embodiment of the diaper 50 has an asymmetric, modified T-shaped absorbent core 540 having ears in the first waist region but a generally rectangular shape in the second waist region. Exemplary absorbent structures for use as the absorbent core of the present invention that have achieved wide acceptance and commercial success are described in U.S. Pat. No. 4,610,678 entitled "High-Density Absorbent Structures" issued to Weisman et al. on Sep. 9, 1986; U.S. Pat. No. 4,673,402 entitled "Absorbent Articles With Dual-Layered Cores" issued to Weisman et al. on Jun. 16, 1987; U.S. Pat. No. 4,888,231 entitled "Absorbent Core Having A Dusting Layer" issued to Angstadt on Dec. 19, 1989; and U.S. Pat. No. 4,834,735, entitled "High Density Absorbent Members Having Lower Density and Lower Basis Weight Acquisition Zones", issued to Alemany et al. on May 30, 1989. The absorbent core may further comprise the dual core system containing an acquisition/distribution core of chemically stiffened fibers positioned over an absorbent storage core as detailed in U.S. Pat. No. 5,234,423, entitled "Absorbent Article With Elastic Waist Feature and Enhanced Absorbency" issued to Alemany et al., on Aug. 10, 1993; and in U.S. Pat. No. 5,147,345, entitled "High Efficiency Absorbent Articles For Incontinence Management" issued to Young, LaVon and Taylor on Sep. 15, 1992. All of these patents are incorporated herein by reference.

The backsheet and the topsheet are positioned adjacent the garment surface and the body surface, respectively, of the absorbent core. The absorbent core is preferably joined with the topsheet, the backsheet, or both in any manner as is known by attachment means (not shown in FIG. 5) such as those well known in the art. However, embodiments of the present invention are envisioned wherein portions of the entire absorbent core are unattached to either the topsheet, the backsheet, or both.

For example, the backsheet and/or the topsheet may be secured to the absorbent core or to each other by a uniform continuous layer of adhesive, a patterned layer of adhesive, or an array of separate lines, spirals, or spots of adhesive. Adhesives which have been found to be satisfactory are manufactured by H. B. Fuller Company of St. Paul, Minn. under the designation HL-1258 or H-2031. The attachment means will preferably comprise an open pattern network of filaments of adhesive as is disclosed in U.S. Pat. No. 4,573,986, issued to Minetola, et al. on Mar. 4, 1986, and which is incorporated herein by reference. An exemplary attachment means of an open pattern network of filaments comprises several lines of adhesive filaments swirled into a spiral pattern such as illustrated by the apparatus and method shown in U.S. Pat. No. 3,911,173 issued to Sprague, Jr. on Oct. 7, 1975; U.S. Pat. No. 4,785,996 issued to Zwieker, et al. on Nov. 22, 1978; and U.S. Pat. No. 4,842,666 issued to Werenicz on Jun. 27, 1989. Each of these patents are incorporated herein by reference. Alternatively, the attachment means may comprise heat bonds, pressure bonds, ultrasonic bonds, dynamic mechanical bonds, or any other suitable attachment means or combinations of these attachment means as are known in the art.

In a preferred embodiment, the diaper 50 further comprises elasticized leg cuffs 550 for providing improved containment of liquids and other body exudates; an elastic waist feature 560 that provides improved fit and containment; and a fastening system 570 which forms a side closure which maintains the first waist region 86 and the second waist region 88 in an overlapping configuration such that lateral tensions are maintained around the circumference of the diaper to maintain the diaper on the wearer. The diaper 50 may also comprise elasticized side panels (not shown) in the waist regions 86 and 88 to provide an elastically extensible feature that provides a more comfortable and contouring fit and more effective application of the diaper 50.

The elasticized leg cuffs 550 can be constructed in a number of different configurations, including those described in U.S. Pat. No. 3,860,003 issued to Buell on Jan. 14, 1975; U.S. Pat. No. 4,909,803, issued to Aziz et al. on Mar. 20, 1990; U.S. Pat. No. 4,695,278, issued to Lawson on Sep. 22, 1987; and U.S. Pat. No. 4,795,454, issued to Dragoo on Jan. 3, 1989, each of which are incorporated herein by reference.

The elasticized waist feature preferably comprises an elasticized waistband (not shown) that may be constructed in a number of different configurations including those described in U.S. Pat. No. 4,515,595 issued to Kievit et al. on May 7, 1985; U.S. Pat. No. 5,026,364 issued to Robertson on Jun. 25, 1991; and the above referenced U.S. Pat. No. 5,151,092 issued to Buell et al. on Sep. 29, 1992, each of which are incorporated herein by reference.

The elasticized side panels may be constructed in a number of configurations. Examples of diapers with elasticized side panels positioned in the ears (ear flaps) of the diaper are disclosed in U.S. Pat. No. 4,857,067, issued to Wood, et al. on Aug. 15, 1989; U.S. Pat. No. 4,381,781, issued to Sciaraffa, et al. on May 3, 1983; U.S. Pat. No. 4,938,753, issued to Van Gompel, et al. on Jul. 3, 1990; and U.S. Pat. No. 5,151,092, issued to Buell et al. on Sep. 29, 1992; each of which are incorporated herein by reference.

Exemplary fastening systems 570 are disclosed in U.S. Pat. No. 4,846,815, issued to Scripps on Jul. 11, 1989; U.S. Pat. No. 4,894,060, issued to Nestegard on Jan. 16, 1990; U.S. Pat. No. 4,946,527, issued to Battrell on Aug. 7, 1990; U.S. Pat. No. 3,848,594, issued to Buell on Nov. 19, 1974; U.S. Pat. No. B1 4,662,875, issued to Hirotsu et al. on May 5, 1987; and U.S. Pat. No. 5,151,092, issued to Buell et al. on Sep. 29, 1992; each of which are incorporated herein by reference.

The diaper 50 is preferably applied to a wearer by positioning one of the waist regions of the diaper, preferably the second waist region 88, under the wearer's back and drawing the remainder of the diaper between the wearer's legs so that the other waist region, preferably the first waist region 86, is positioned across the front of the wearer. The fastening system is then applied to effect a side closure.

The absorbent composite webs of the present invention are also useful in training pants. The term "training pants", as used herein, refers to disposable garments having fixed sides and leg openings. Training pants are placed in position on the wearer by inserting the wearer's legs into the leg openings and sliding the training pant into position about the wearer's lower torso. Suitable training pants are disclosed in U.S. Pat. No. 5,246,433, issued to Hasse, et al. on Sep. 21, 1993 which is incorporated herein by reference.

Another disposable absorbent article for which the absorbent composite webs of the present invention are useful are incontinence articles. The term "incontinence article" refers to pads, undergarments (pads held in place by a suspension system of the same type, such as a belt, or the like), inserts for absorbent articles, capacity boosters for absorbent articles, briefs, bed pads, and the like regardless of whether they are worn by adults or other incontinent persons. Suitable incontinence articles are disclosed in U.S. Pat. No. 4,253,461 issued to Strickland, et al. on Mar. 3, 1981; U.S. Pat. Nos. 4,597,760 and 4,597,761 each issuing to Buell on Jul. 1, 1986; U.S. Pat. No. 4,704,115 issued to Buell on Nov. 3, 1987; U.S. Pat. No. 4,909,802 issued to Ahr, et al.; U.S. Pat. No. 4,964,860 issued to Gipson, et al. on Oct. 23, 1990; and in U.S. patent application Ser. No. 07/637,090 filed by Noel, et al. on Jan. 3, 1991 (PCT Publication No. WO 92/11830 published on Jul. 23, 1992).

The Process

The absorbent composite web 10 or fluid handling member 100 herein is formed through a preferred process comprising the steps of delivering a first set of fibers, preferably being moisture-insensitive, to a patterned screen having a plurality of raised and recessed portions. Next, the first set of fibers are laid onto the patterned screen similar to the one seen in FIG. 2 to form a primary material having a top surface, a bottom surface and a plurality of apertures extending from the top surface to the bottom surface of the primary material. The formed apertures correspond to the raised portions on the patterned screen. Once the apertures have been formed, the primary material and patterned screen are separated from one-another. The apertures of the primary material are then filled with a second set of fibers. Once the apertures 25 are filled, this second set of fibers then preferably forms a layer of a secondary material that lays on the bottom surface of the primary material. That is, the secondary material is positioned adjacent to the bottom surface of the primary material. Lastly, the primary material and the secondary material may be bonded to one-another preferably through heating to form a thermally bonded, multi-layered absorbent composite or web. In another process, the bonding step to bond the primary and secondary materials together may be accomplished through any of the other conventional means for joining webs together such as adhesives, pressure bonds, ultrasonic bonds, dynamic mechanical bonds, crimping or any other suitable attachment means or combinations of these attachment means as are known in the art.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A web, comprising:
a first material having a top surface, a bottom surface, and a plurality of apertures extending from said top surface to said bottom surface, said first material having a density gradient; and
a second material having an upper surface and a lower surface, said second material upper surface being positioned adjacent to said first material bottom surface, said second material extending into said plurality of apertures in said first material.

2. The web of claim 1 wherein said first material is less dense towards said top surface and more dense towards said bottom surface.

3. The web of claim 1 wherein said density gradient is provided by one or more of the group selected from: compacting fibers within said first material and forming said primary material from fibers of varying denier.

4. The web of claim 1 wherein said second material includes a density gradient.

5. The web of claim 4 wherein said second material is less dense towards said upper surface and more dense towards said lower surface.

6. The web of claim 1 wherein said second material comprises cellulosic material.

7. The web of claim 1 wherein said second material comprises synthetic material.

8. The web of claim 1 wherein said first material is selected from the group consisting of mono-component fibers and bi-component fibers.

9. The web of claim 1 wherein said first material further comprises a wetting agent.

10. The web of claim 1 wherein said first material comprises a fluid-acquiring foam and said second material comprises fluid-absorbing foam.

11. The web of claim 1 wherein said web further comprises a third material having a top surface placed immediately adjacent to said lower surface of said second material and a bottom surface positioned opposite of said top surface of said third material.

12. A disposable absorbent article, comprising:
a chassis having an upper surface and a bottom surface, a front portion, a back portion positioned opposite to said front portion, a crotch portion positioned between said front portion and said back portion, a longitudinal axis, a transverse axis, a pair of end edges and a pair of longitudinal edges, said chassis comprising:

a topsheet;

a backsheet joined to said topsheet, said backsheet having an inner surface and an outer surface; and a fluid handling member positioned between said topsheet and said backsheet, said fluid handling member comprising a first material having a top surface, a bottom surface, and a plurality of apertures extending from said top surface to said bottom surface; and a second material having an upper surface and a lower surface, said second material upper surface being positioned adjacent to said first material bottom surface, said second material extending into said plurality of apertures in said first material;

wherein said first or second material includes a density gradient.

13. A web, comprising:

a first material having a top surface, a bottom surface, and a plurality of apertures extending from said top surface to said bottom surface; and a second material having an upper surface and a lower surface, said second material having a density gradient, said second material upper surface being positioned adjacent to said first material bottom surface, said second material extending into said plurality of apertures in said first material.

14. The web of claim 13 wherein said second material is less dense towards said top surface and more dense towards said bottom surface.

15. The web of claim 13 wherein said density gradient is provided by one or more of the group selected from: compacting fibers within said first material and forming said primary material from fibers of varying denier.

16. The web of claim 13 wherein said second material comprises cellulosic material.

17. The web of claim 13 wherein said second material comprises synthetic material.

18. The web of claim 13 wherein said first material is selected from the group consisting of mono-component fibers and bi-component fibers.

19. The web of claim 13 wherein said first material further comprises a wetting agent.

20. The web of claim 13 wherein said first material comprises a fluid-acquiring foam and said second material comprises fluid-absorbing foam.

21. The web of claim 13 wherein said web further comprises a third material having a top surface placed immediately adjacent to said lower surface of said second material and a bottom surface positioned opposite of said top surface of said third material.

* * * * *